United States Patent [19]
Lindauer et al.

[11] Patent Number: 4,731,243
[45] Date of Patent: Mar. 15, 1988

[54] ANTIPERSPIRANT AND/OR DEODORANT STICK HAVING SUSPENDED THEREIN FRAGRANCE-CONTAINING POLYMERIC PARTICLES

[75] Inventors: Jerome I. Lindauer, Hillsdale, N.J.; Sharon L. Reich, Briarwood; Rose L. Trizzino, Staten Island, both of N.Y.; Valerie M. Suran, Kingston; David E. Cincotta, South Orange, both of N.J.

[73] Assignee: International Flavors & Fragrances Inc., New York, N.Y.

[21] Appl. No.: 829,484

[22] Filed: Feb. 14, 1986

Related U.S. Application Data

[63] Continuation-in-part of Ser. No. 662,681, Oct. 19, 1984.

[51] Int. Cl.[4] .............................................. A61K 7/32
[52] U.S. Cl. ................................. 424/65; 424/DIG. 5
[58] Field of Search ...................... 241/3, 23, DIG. 37; 252/522 A; 264/178 R; 424/DIG. 5, 65

[56] References Cited

U.S. PATENT DOCUMENTS

| | | | |
|---|---|---|---|
| 4,217,426 | 8/1980 | McConnell et al. | 264/178 R |
| 4,252,789 | 2/1981 | Broad | 424/DIG. 5 X |
| 4,521,541 | 6/1985 | Rutherford et al. | 264/50 X |
| 4,524,062 | 6/1985 | Laba et al. | 424/65 |
| 4,673,571 | 6/1987 | Mahieu et al. | 424/DIG. 5 X |

OTHER PUBLICATIONS

Spice Quality: Effect of Cryogenic and Ambient Grinding on Volatiles, C. A. Pesek, L. A. Wilson, and E. G. Hammond.

Primary Examiner—P. W. Echols
Assistant Examiner—Joseph M. Gorski
Attorney, Agent, or Firm—Arthur L. Liberman

[57] ABSTRACT

Described are deodorant and/or antiperspirant sticks which contain suspended therein fragrance-containing polymeric pellets containing 1 to 80% fragrance, the polymeric pellets produced by means of cryogenically grinding an extruded mixture of perfume composition and polymer.

6 Claims, 9 Drawing Figures

FIG.7
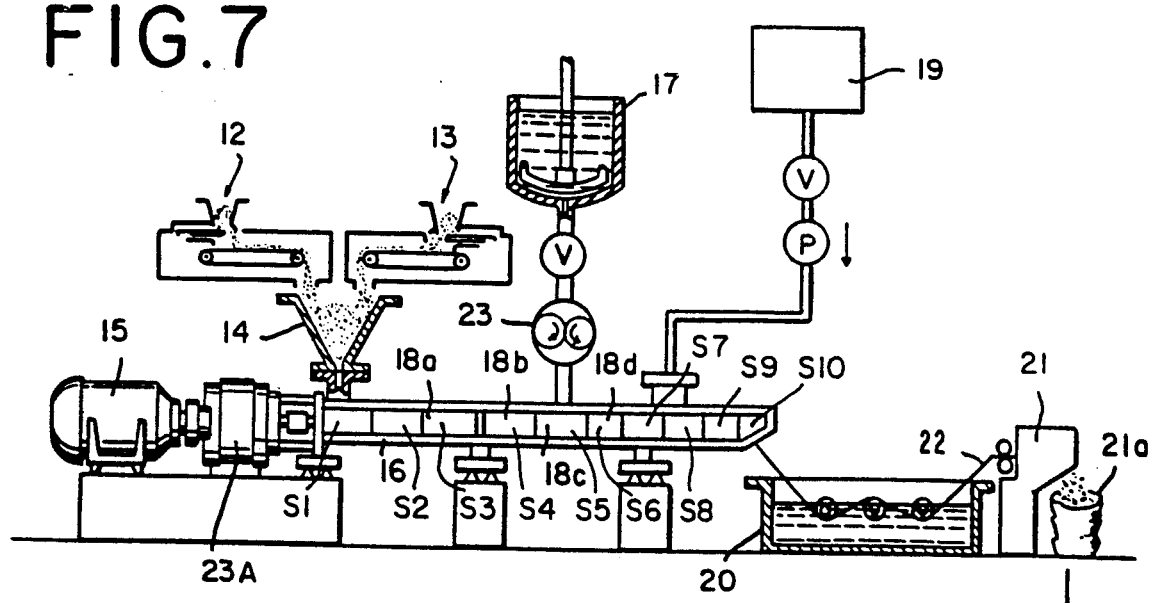
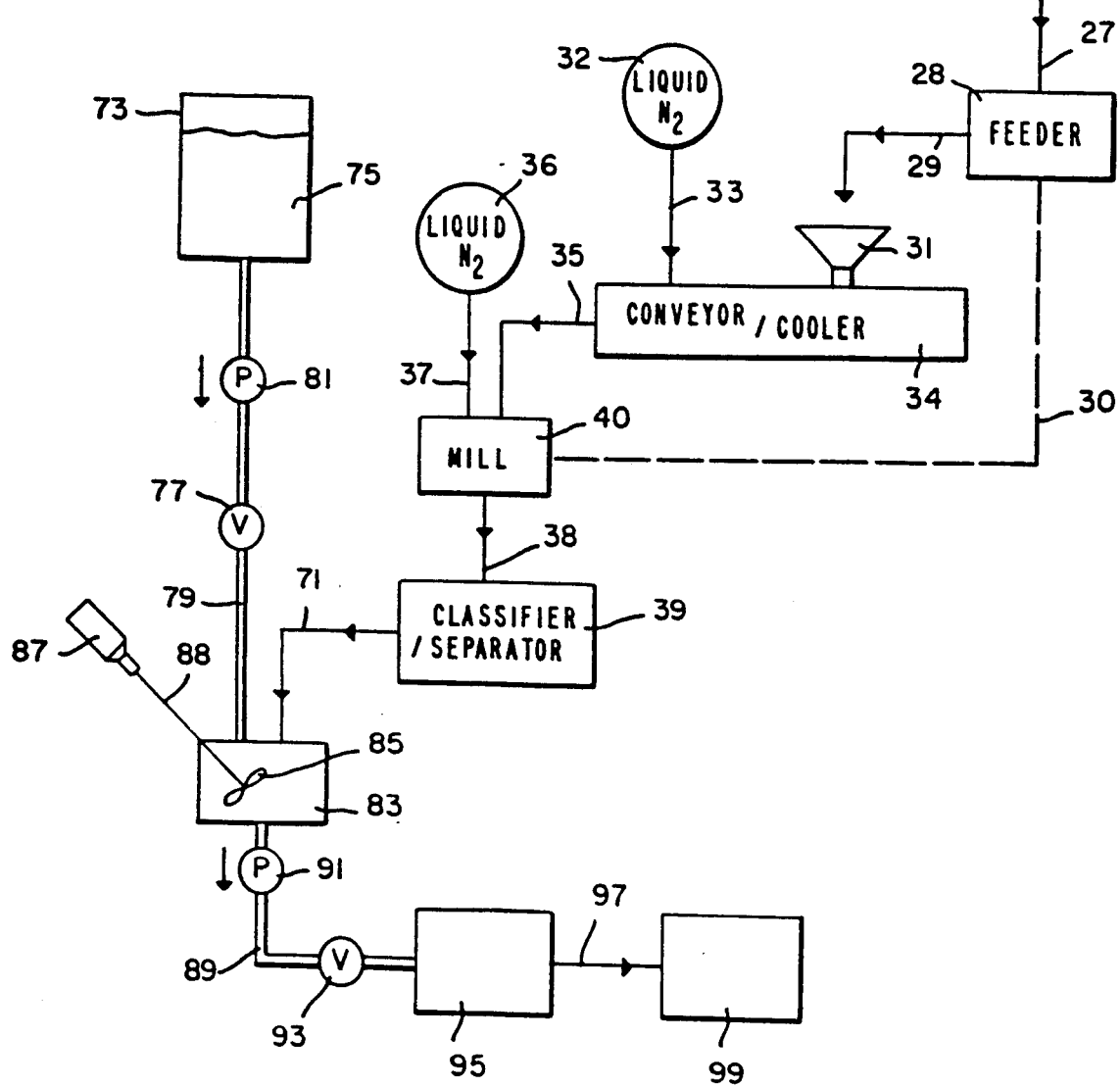

ANTIPERSPIRANT AND/OR DEODORANT STICK HAVING SUSPENDED THEREIN FRAGRANCE-CONTAINING POLYMERIC PARTICLES

This application is a continuation-in-part of application for U.S. Letters Patent Ser. No. 662,681 filed on Oct. 19, 1984.

BACKGROUND OF THE INVENTION

A commercial and social need exists for a long lasting deodorant or deodorant/antiperspirant vehicle having a pleasant or aesthetically pleasing fragrance. Several attempts at producing fragrance longevity for antiperspirant and deodorant products have been attempted in the prior art including encapsulation and spray drying. All of the methods of the prior art have produced negative or inconsistent results, for example, encapsulation requires complete rupturing of the capsule wall to achieve fragrance release and spray drying requires a breakdown of the starch/gum matrix which is the spray dried material by means of introduction thereto of moisture at a particular range of temperature and humidity. Indeed, "fragrance fixation" produces distortion of the fragrance profile and liquid polymers generally present incompatibility problems with the fragrance.

U.S. Pat. No. 4,217,426 issued on Aug. 12, 1980 discloses a semi-crystalline polyester/low viscosity polyethylene melt blend, which is non-tacky and non-blocking and readily grindable by means of cryogenic grinding techniques, for providing powders suitable for powder adhesives particularly useful for fusible interlinings or for providing powder coating materials.

Nothing in U.S. Pat. No. 4,217,426 discloses the utility of the cryogenically ground polymer for use in the fragrance area or for use in the long lasting deodorant or deodorant/antiperspirant area.

OBJECTS OF THE INVENTION

It is an object of our invention to achieve long lasting deodorancy using a fragrance when a fragrance is incorporated into a solid antiperspirant or deodorant vehicle.

It is a further object of our invention to provide a long lasting deodorant or fragranced antiperspirant vehicle (with long lasting fragrance) containing polymeric particles which have incorporated therein high loadings of fragrance.

SUMMARY OF THE INVENTION

Our invention relates to long lasting deodorant or fragranced antiperspirant vehicles (with long lasting fragrances) which contain in suspension polymeric particles of the order of 10 up to 500 microns in diameter which contain from about 1% up to about 80% fragrance based on the total weight of the polymeric particle. Such polymeric particles are produced by means of the process of first extruding a mixture of fragrance and polymer and quickly chilling the extrudate through a pelletizing operation and into an inert cooling liquid having a temperature in the range of from about 5° C. up to about 60° C.; then cryogenically grinding the resultant product using liquid nitrogen, liquid air or other cryogenic cooling agent at a pressure in the range of from about 1 atmosphere up to about 50 atmospheres. The cryogenically ground powder is then introduced into the suspension agent which contains, inter alia, hydrocarbon waxes and mineral oils and which also contain from about 2% up to about 8% by weight of the fragrance-containing polymeric particle produced as indicated above.

A critical aspect of our invention resides in the fact that the fragrance-containing polymer which has been cryogenically ground has a density approximating the density of the surrounding suspending agent during processing thereof from that point in time commensing with the inclusion of the cryogenically ground perfume-containing polymer in the suspending material to that point in time when the deodorant and/or antiperspirant sticks containing the fragranced polymer are solidified. Accordingly, the average particle size of the cryogenically ground fragrance-containing polymer should be between 50 and 225 microns; most preferably between 75 and 180 microns.

BRIEF DESCRIPTION OF THE DRAWINGS

FIGS. 5 and 7 are schematic block flow diagrams of apparatus useful in effecting the process of our invention commencing with extrusion and simultaneous foaming of the polymer-perfume mixture; pelletinzing of the extrudate and proceeding to the cryogenic grinding of the resulting extruded pellets followed by suspension of the cryogenically ground polymer-perfume mixture in the deodorant and/or antiperspirant vehicle.

DETAILED DESCRIPTION OF THE INVENTION

Referring to FIGS. 1, 5, 6 and 7, a deodorant vehicle or deodorant/antiperspirant vehicle containing fragrance containing polymeric particles in suspension is produced in the apparatus shown and collected in container 95 and then marketed via route 97 to market 99.

Figure 5:
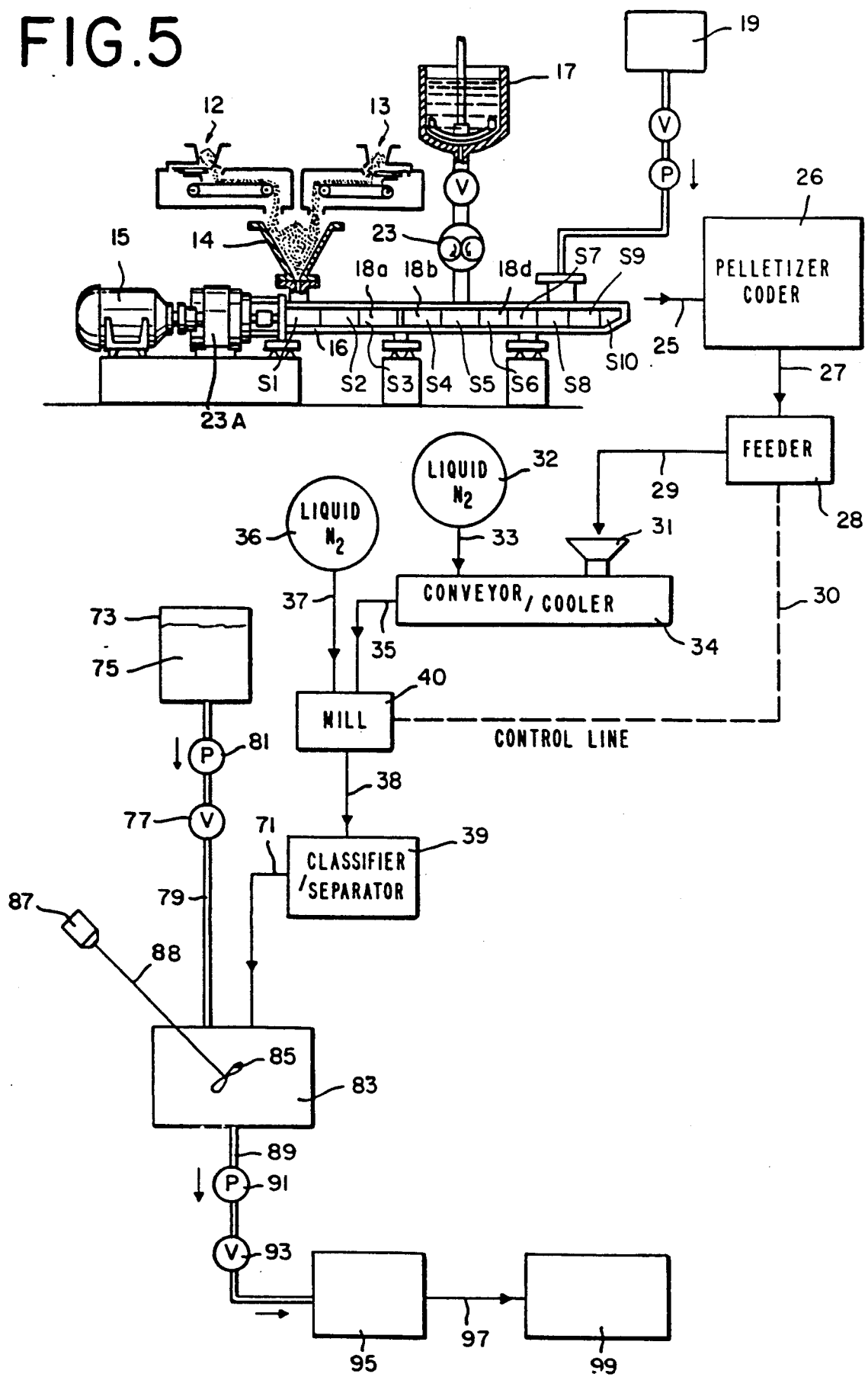
Figure 6:
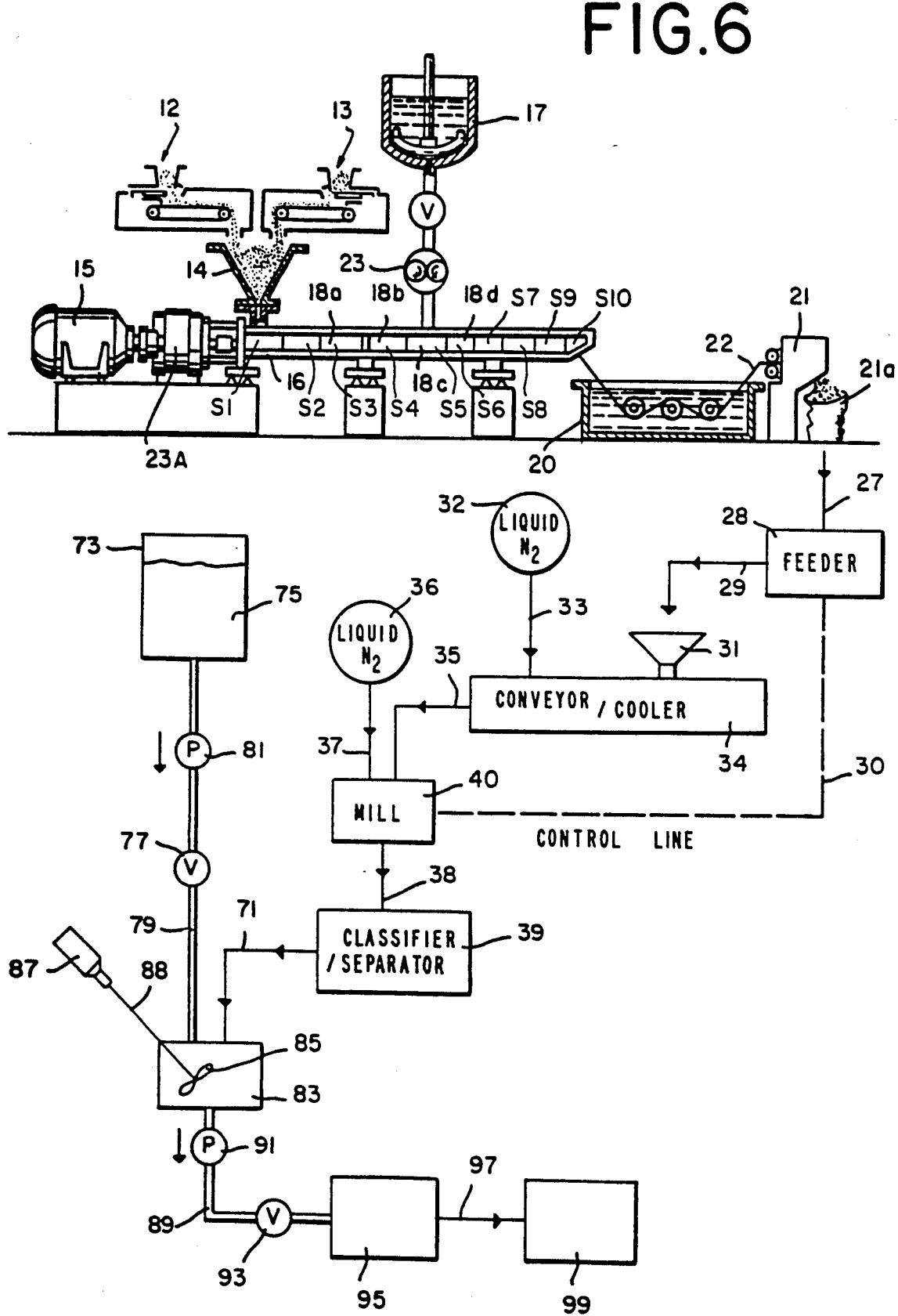

FIGS. 1, 5, 6 and 7 are schematic cut-away elevation diagrams of the apparatus useful in carrying out the process of our invention during the operation of said apparatus. Motor 15 drives the extruder screws located at 23A in barrel 16, the extruder being operated at temperatures in the range of from about 150°0 up to about 250° C. At the beginning of the barrel, resin at source 12 optionally together with additives, e.g., or pacifiers, processing aids, colors, pearlescent agents and densifiers at location 13 is added via addition funnel 14 into the extruder. Simultaneously (when the operation reaches "steady state"), fragrance material is added to the extruder at 1, 2 or more of barrel segments 3–8 (shown as S3, S4, S5, S6, S7 and S8 in FIGS. 1, 5, 6 and 7) of the extruder (which may be a twin screw or single screw extruder) at locations 18a, 18b, 18c and 18d by means of gear pump 23 from source 17. Optionally, from source 19 (shown only in FIGS. 5 and 7) into barrel segments 5–10 (shown as S5, S6, S7, S8, S9 and S10 in FIGS. 1, 5, 6 and 7), gaseous or liquid blowing agents, e.g., nitrogen, carbon dioxide and the like may be optionally added simultaneously with the addition of the fragrance. The feed rate range of resin is about 80–300 pounds per hour. The feed rate range of the fragrance is between 1.01 and 400% of the feed rate range of the resin. In the event that a blowing agent is used, the blowing agent rate range is such that the pressure of the gas or the pressure over the liquid being fed into the extruder is between about 50 and 200 psig. If desired (as shown in FIGS. 6 and 7) the extruded ribbon or cylinder may be passed through water bath 20 and pelletizer 21 into collection apparatus 21a. The water cooling and pelletizing operation may be carried out in any conventional pelletizer 26 with extrudate tow entering through line 25 and leaving through line 27.

The resulting pellets are passed into feeder 28 which is controlled through control line 30 insofar as the rate of feeding into hopper 31 is concerned (depending upon the rate of operation of the cryogenic mill 40). The resulting pellets are then passed into conveyor/cooler 34 where they are cooled in a direct contact fashion with liquid nitrogen being passed into the conveyor/cooler from holding tank 32 through line 33. The cryogenically cooled pellets are then passed through line 35 into mill 40 which is also cooled using liquid nitrogen from tank 36 through line 37. As stated, supra, the rate of operation of the mill controls the rate of operation of the feeder for feeding the pellets coming from the pelletizer 26 into hopper 31. The milled polymeric particles are then passed through line 38 into classifier/separator 39 where the particles are classified and sorted and groups of particles having various diameter ranges are used for the purpose of incorporation into deodorant and/or antiperspirant sticks.

Figure 1:
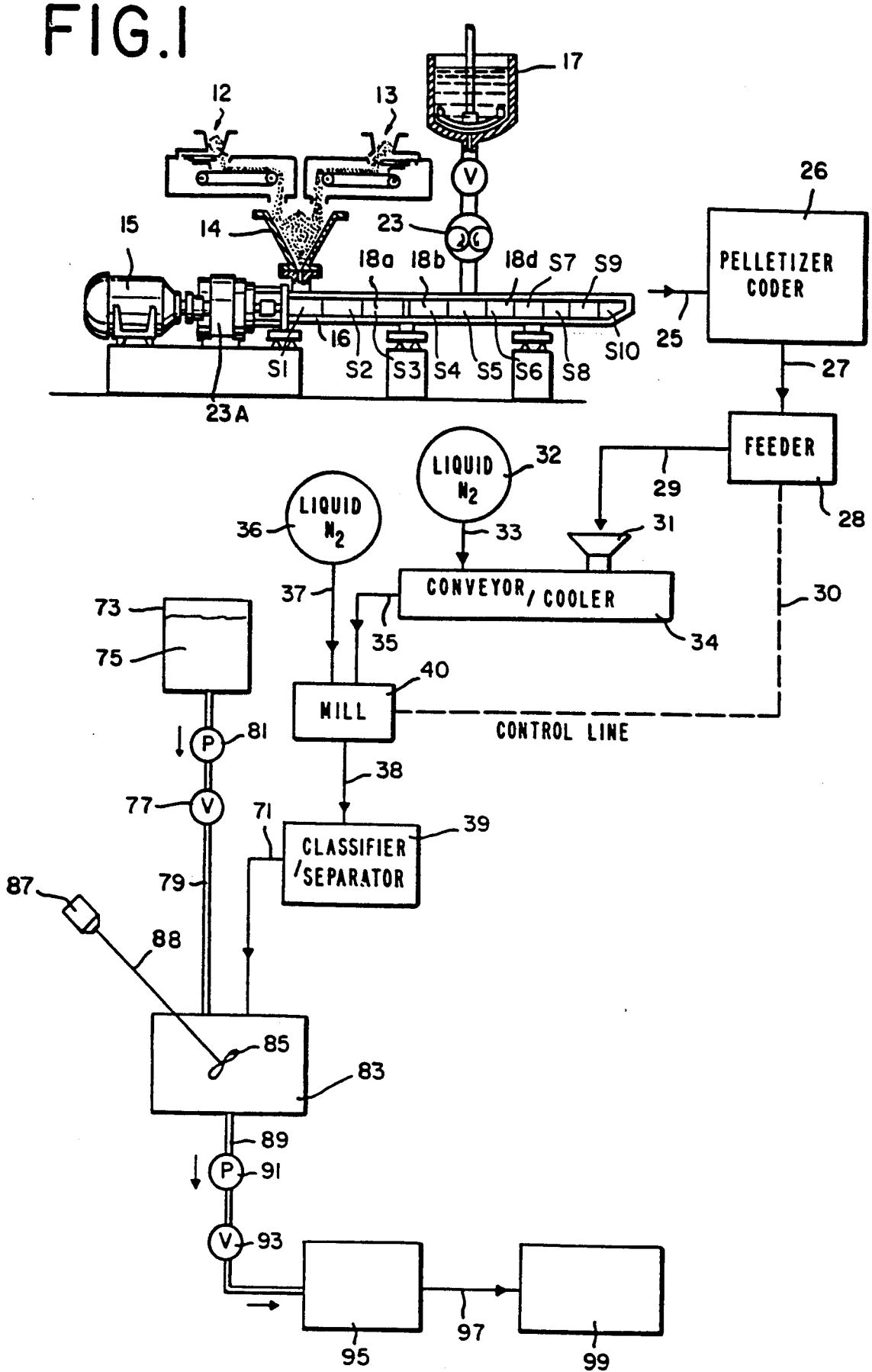
FIGS. 1 and 6 are schematic block flow diagrams of the apparatus useful in effecting the process of our invention commencing with extrusion of the polymer-perfume mixture, pelletizing of the extrudate and proceeding to the cryogenic grinding of the resulting extruded pellets followed by suspension of the cryogenically ground polymer perfume mixture in the deodorant and/or antiperspirant vehicle.
Figure 2:
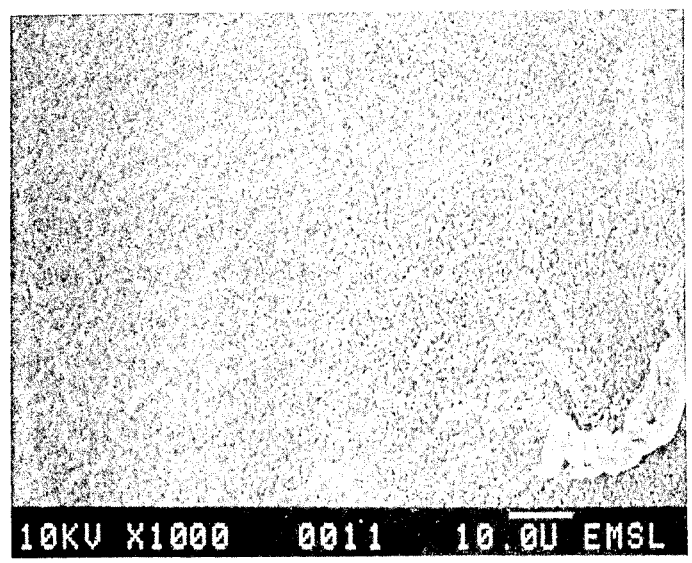
FIG. 2A is an electron micrograph (1000×) of extruded polymer-fragrance mixture containing 60% fragrance prior to cryogenically grinding.
FIG. 2B is an electron micrograph of the same substance as in FIG. 2A except the electron micrograph is 10,000×.
Figure 2:
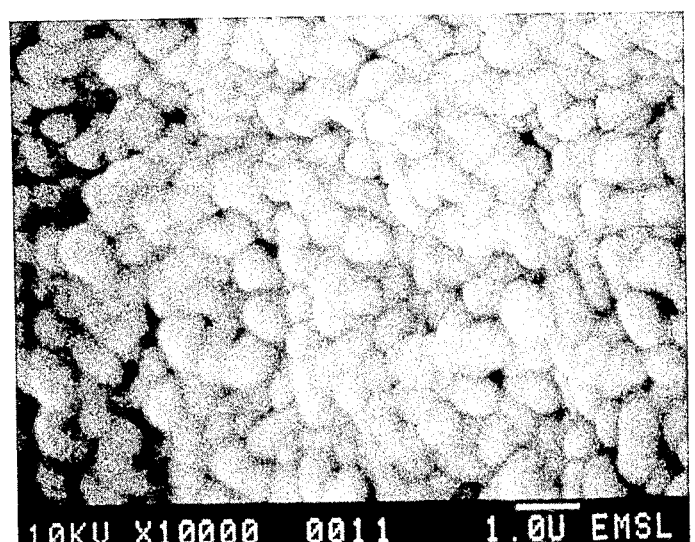
Figure 3A:
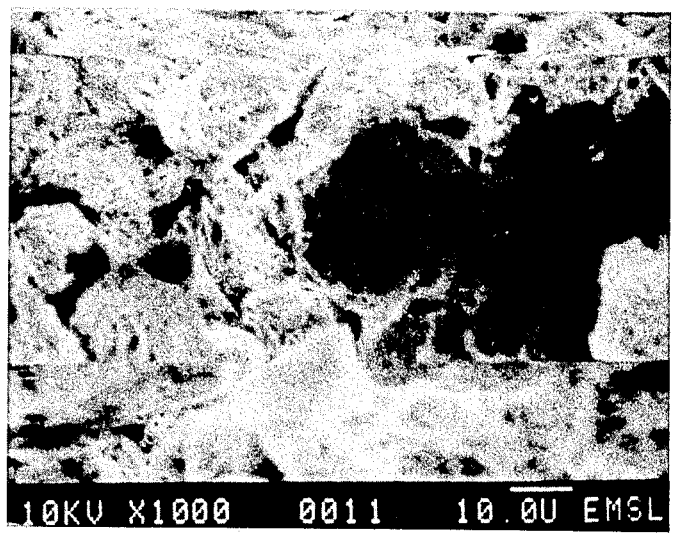
FIG. 3A is an electron micrograph (1000×) of a section of a cryogenically ground extruded tow of polymer containing 60% by weight of fragrance of Example I.
Figure 3B:
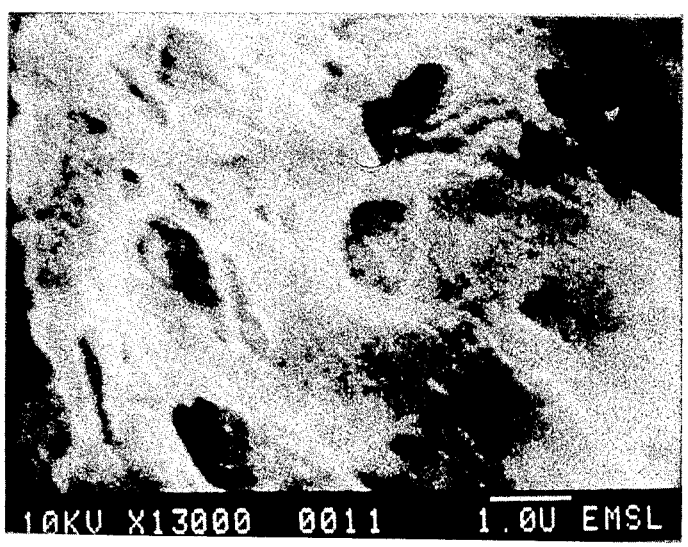
FIG. 3B is an electron micrograph of the same substance as FIG. 3A (Example I) except that the electron micrograph is 13,000×.
Figure 4:
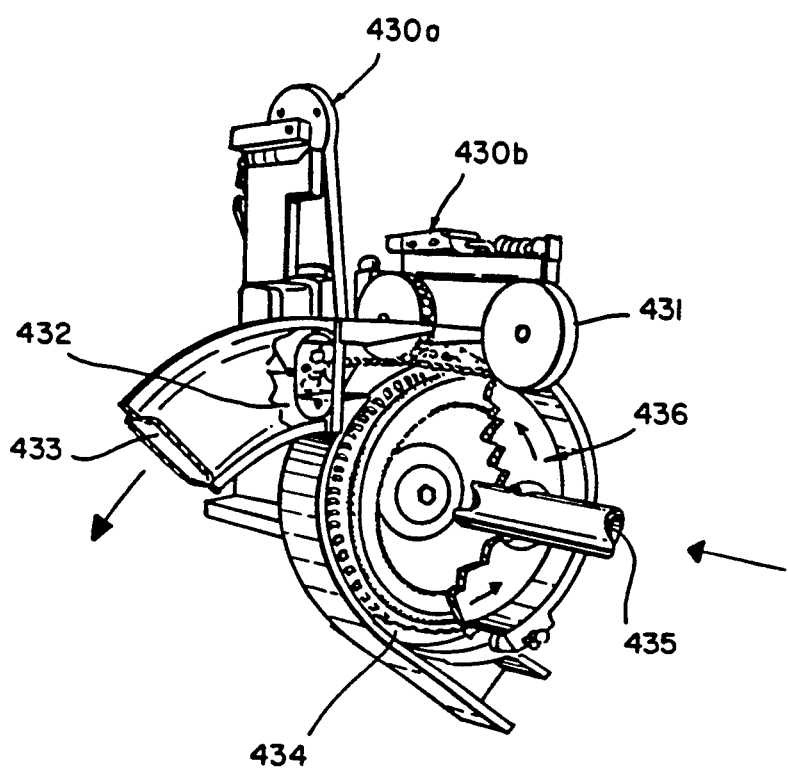
FIG. 4 is a cut-away perspective diagram of a pelletizing apparatus used in conjunction with the extrusion apparatus, for example, that illustrated in FIG. 1 whereby the extruded tow is pelletized.

FIG. 4 is a detailed cut-away perspective view of such a pelletizer as is used in conjunction with the apparatus of FIGS. 1 and 5. The extruded material coming from the extruder is fed into pelletizer at zero pressure at location 434. The pelletizer is operated using a spinning extrusion die 436 and operated by means of a rotating wheel 434. Moving pellet knife 431 and dual knife units 430a and 430b cause pellets to be formed which fly into a cooling water stream 432. The resulting pellets which are formed and contain fragrance exit from the pelletizer at 433.

The cryogenically ground perfume bearing particles are passed through line 71 into mixing vessel 83 wherein agitator 85 powered from source 87 using shaft 88 blends the cryogenically ground fragrance-containing polymer with deodorant and/or antiperspirant/deodorant suspension vehicle 75 held in tank 73 and passed through line 79 using pump 81 past valve 77. The thus-blended vehicle containing from about 2% up to about 8% by weight of cryogenically ground fragrance bearing polymer is then passed through slurry conveyance line 89 using pump 91 past valve 93 into apparatus 95 which forms the thus-created liquid into deodorant and/or antiperspirant sticks and where the thus-formed sticks are packaged ready for market through channel of distribution 97 to market 99.

Our invention incorporates by reference the invention covering the process for forming the cryogenically ground perfume bearing polymeric particles filed on Oct. 19, 1984 in the names of Howard John Rutherford, Donald Arthur Withycombe and Lloyd F. Keleher (U.S. Letters Patent Ser. No. 662,682).

The nature of the extruder utilized in the process useful in conjunction with our invention to form fragrance-containing polymer particles may be either single screw or double screw. Double screw extruders are preferred. Thus, the types of extruders that can be used are disclosed at pages 246–267 and 332–349 of the Modern Plastics Encyclopedia, 1982–1983, published by the McGraw Hill Publishing Company, the disclosure of which is incorporated by reference herein. More specifically, examples of extruders which are useable in carrying out the process of our invention (with modification for introduction of fragrance downstream from introduction of the polymer and with a further optional modification that the gaseous blowing agent may be introduced still further downstream from the point of introduction of the fragrance) are as follows:

1. The Welex "Super Twinch" 3.5 inch extruder manufactured by the Welex Incorporated, 850 Jolly Road, Blue Bell, Pa. 19422.
2. Krauss-Maffei twin screw extruder manufactured by the Krauss-Maffei Corporation/Extruder Division, 3629 West 30th Street South, Wichita, Kans. 67277.
3. Modified Sterling Model 4000 and 5000 series extruder manufactured by Sterling Extruder Corporation of 901 Durham Avenue, South Plainfield, N.J.
4. CRT ("Counter-Rotating Tangential") Twin Screw Extruder manufactured by Welding Engineers, Inc. of King of Prussia, Pa. 19406.
5. The Leistritz Twin Screw Dispersion Compounder manufactured by the American Leistritz Extruder Corporation of 198 U.S. Route 206 South, Somerville, N.J. 08876.
6. The ZSK Twin Screw Co-Rotating Extruder manufactured by the Werner & Pfleiderer Corporation of 663 East Crescent Avenue, Ramsey, N.J. 07446.
7. The Farrel Extruder manufactured by the Farrel Connecticut Division, Emhart Machinery Group, Ansonia, Conn. 06401.
8. The MPC/V Baker Perkins Twin Screw Extruder manufactured by the Baker Perkins Inc. Chemical Machinery Division of Saginaw, Mich. 48601.
9. The Berstorff single screw, twin screw, or foam extrusion equipment manufactured by the Berstorff Corporation, P. O. Box 240357, 8200-A Arrowridge Buolevard, Charlotte, N.C. 28224.
10. The Leistritz laboratory extruder system LSM 30.34 manufactured by the American Leistritz Extruder Corporation of 198 U.S. Route 206 South, Somerville, N.J. 08876.

When producing fragrance-containing polymer particles useful in conjunction with our invention, various polymers may be utilized, for example, low density polyethylene, high density polyethylene, co-extruded high molecular weight high density polyethylene with low density polyethylene (reference: *Modern Plastics,* January 1986 page 76 incorporated by reference herein), polypropylene, polyvinyl chloride and co-polymers of ethylene and a vinyl monomer selected from the group consisting of (a) vinyl acetate; (b) ethyl acrylate; (c) methyl acrylate; (d) butyl acrylate; and (e) acrylic acid as well as the hydrolyzed co-polymer of ethylene and vinyl acetate. Preferred co-polymers are ethylene/vinyl acetate with about 9 to 60% vinyl acetate and ethylene/ethyl acrylate with about 6 to 18% ethyl acrylate.

Resins of the type disclosed for use as co-polymers are commercially available in the molding powder form. For example, ethylene vinyl acetate co-polymers are marketed by the E. I. duPont de Nemours Company under the tradename "ELVAX ®" and by the Arco Polymer Division under the trademark "DYLAND ®" and by the Exxon Corporation of Linden, N.J. under the trademark "DEXXON ®". Ethylene/ethyl acrylate co-polymers are marketed by Union Carbide Corporation under the tradename "EEA RESINS ®".

The polymer is added to the single screw or twin screw extruder at a feed rate in the range of from about 80 up to about 300 pounds per hour while maintaining the temperature in the screw extruder between about 160° and about 240° C. If the polymer or co-polymer powder is added to the extruder at a reference "barrel segment", then the fragrance substance is added to the extruder under pressure downstream from the addition point of the polymer at 1 or more "barrel segments" 2–9 (shown as S2, S3, S4, S5, S6, S7, S8 and S9 in FIGS. 1, 5, 6 and 7).

Thus, the invention provides a process for forming polymeric pellets which include a relatively high concentration of fragrance material. The fragrance material is added at "barrel segments" 2–9 (shown as S2, S3, S4, S5, S6, S7, S8 and S9 in FIGS. 1, 5, 6 and 7) of the single screw or twin screw extruder and must be previously or made to be compatible with the polymer added at "barrel segment" 1 (shown as S1 in FIGS. 1, 5, 6 and 7) of the single screw or twin screw extruder.

The nature of the cryogenic grinding apparatus useful in the practice of our invention is exemplified by several of those set forth in "Plastics Technology/Manufacturing Handbook and Buyers' Guide", Volume 30, No. 7, Mid-June 1984, pages 234, 240, 242 and 243, published by the Bill Publication Corporation of New York, N.Y. and are exemplified as follows:
1. The "CRYO-GRIND ®" cryogenic grinding system manufactured by the Air Products and Chemicals Inc. of Allentown, Pa.
2. Cryogenic Pulverizers manufactured by Pallmann Pulverizers Co., Inc.
3. Wedco cryogenic pulverizing system manufactured by Wedco, Inc.

This invention can be further illustrated by the following examples of preferred embodiments thereof, although it will be understood that these examples are included merely for purposes of illustration and are not intended to limit the scope of the invention unless otherwise specifically indicated.

EXAMPLE I

High density polyethylene is extruded in a Hoake Plasticorder with perfume containing the following ingredients:

| INGREDIENTS | PARTS BY WEIGHT |
| --- | --- |
| Galaxolide 50% | 41.4 |
| The formic acid ester of α-hydroxy ethyl-3,3-dimethyl-cyclohexane | 18.4 |
| p-t-Butyl Cyclohexyl Acetate | 18.4 |
| Peach Aldehyde | 9.2 |
| Prenyl Acetate | 3.2 |
| Bicyclopentadiene Propionate | 3.2 |
| Amyl Butyrate | 4.3 |
| Ethyl Isovalerate | 4.2 |
| Ethyl Tiglate | 4.4 |
| Menthone | 8.2 |
| Ethylmethylphenyl Glycidate | 3.2 |
| Allylcyclohexyl Propionate | 4.1 |
| Ethyl Cinnamate | 3.2 |
| Isocyclocitral | 12.3 |

The percentage of fragrance in the polyethylene is 60%. The resulting tow is quickly chilled in a liquid quenching medium (water at 5° C.) and pelletized. The resulting pellets containing fragrance are then cryogenically ground using liquid nitrogen to achieve an average particle size of 100 microns.

A wax-type deodorant stick formulation having the following formula is prepared:

| INGREDIENTS | PARTS BY WEIGHT |
| --- | --- |
| ARISTOWAX ® 165 (Registered Trademark of Witco Chemical Corporation for Paraffin Wax) | 14.0 |
| Ozokerite Wax 170-d (hydrocarbon wax) | 8.0 |
| White Petrolatum | 13.0 |
| ACETULAN ® (Acetylated Lanolin Alcohol manufactured by Amerchol Chemical Company | 2.8 |
| Diisopropyl Adipate | 6.0 |
| Mineral Oil | 52.1 |
| Propyl Paraben | 0.1 |

The resulting composition is heated to 75° C. until melted. With stirring, 4.0 parts by weight of cryogenically ground polymer as prepared, supra, containing the fragrance as set forth, supra, is added to the wax deodorant stick formulation while maintaining the temperature at 75° C. The resulting mixture is stirred in order to ensure a uniform suspension of the cryogenically ground polymer perfume containing particles in the deodorant stick formulation.

The resulting suspension is then poured into stick molds thereby formulating wax deodorant sticks containing cryogenically ground polymer particles suspended therein, each stick being cylindrical and having a length of three inches and a diameter of one inch.

A panel test was conducted on 30 independent panelists to determine which product produced the strongest fragrance after 8 hours. Of the 30 panel members, 25 panelists (83.3%) perceived the fragrance produced from the cryogenically ground fragrance containing polymer to be twice as strong; 3 of the panelists thought that the fragrance not included in the cryogenically ground polymer was somewhat stronger than the other fragrance and 2 of the panelists thought that neither fragrance was stronger than the other. These results are statistically significant at a 99.9% confidence level.

EXAMPLE II

Deodorant Stick

A deodorant stick composition is prepared containing the following materials:

| INGREDIENTS | PARTS BY WEIGHT |
|---|---|
| Propylene Glycol | 65.00 |
| Sodium Stearate | 7.00 |
| Distilled Water | 23.75 |
| IRGASAN ® DP-300 (2,4,4-Trichloro-2'-Hydroxy Diphenyl Ether, manufactured by the Ciba-Geigy Chemical Company and a Trademark of the Ciba-Geigy Chemical Company) | 0.25 |

The ingredients are combined and heated to 75° C. with stirring. The ingredients are mixed and continued to be heated until the sodium stearate has dissolved.

The resulting mixture is cooled to 40° C. and while maintaining the mixture at 40° C. cryogenically ground fragrance containing polymer produced according to Example I containing 60% fragrance is added to the formulation. The average particle size is 140 microns.

The resulting suspension is poured into stick molds at 40° C. The resulting stick molds are then cooled to 15° C. The molds are removed from the deodorant sticks which are cylindrical, three inches in length and one inch in diameter.

The resulting deodorant sticks are unanimously preferred by a panel of 30 panelists of the same deodorant sticks with an equal amount of the same fragrance without the fragrance being incorporated into the polymer as set forth above.

What is claimed is:

1. A deodorant or antiperspirant solid suspension comprising a deodorant or antiperspirant-containing suspension agent selected from the group consisting of:
   (i) hydrocarbon wax; and
   (ii) sodium stearate
and suspended therein perfume-containing thermoplastic polymer particles having an average particle size of between 50 and 225 microns, said thermoplastic polymer being selected from the group consisting of:
   (1) low density polyethylene;
   (2) high density polyethylene;
   (3) co-extruded high molecular high density polyethylene and low density polyethylene;
   (4) polypropylene;
   (5) a co-polymer of ethylene and vinyl acetate;
   (6) polyvinyl chloride;
   (7) a copolymer of ethylene and ethyl acrylate;
   (8) a copolymer of ethylene and methyl acrylate;
   (9) a copolymer of ethylene and butyl acrylate;
   (10) a copolymer of ethylene and acrylic acid; and
   (11) the hydrolyzed co-polymer of ethylene and vinyl acetate
said polymeric particles containing from 1 up to about 80% by weight of perfume, said polymeric particles being produced according to the process comprising the steps of:
   (i) co-extruding the thermoplastic polymer with from about 1% up to about 80% of said perfume thereby forming an extrudate with the polymer feed rate range being from 80 up to 300 pounds per hour and the feed rate range of perfume being between 1.01% and 400% of the feed rate range of thermoplastic polymer;
   (ii) quick-chilling said extrudate by contacting said extrudate with an inert cooling liquid at a temperature of from about 5° C. up to about 60° C. whereby extrudate pellets are formed;
   (iii) cryogenically grinding the resulting extrudate pellets to a particle size of from about 10 up to about 500 microns and an average particle size of between 50 and 225 microns thereby forming cryogenically ground extrudate pellets;
   (iv) intimately admixing the resulting cryogenically ground extrudate pellets with said deodorant-containing suspension composition or said antiperspirant-containing suspension composition whereby a liquid suspension is formed; and
   (v) forming the thus created liquid suspension into deodorant or antiperspirant sticks.
the weight percent of cryogenically ground polymer in the resulting suspension being from about 2% up to about 8%, the resulting polymeric particles in said suspension being capable of controlled release of said perfume therefrom into and through the resulting deodorant sticks or anti-perspirant sticks.

2. The product defined according to claim 1 wherein in the process, the step (iii) of cryogenically grinding includes the step of direct treatment of the extrudate pellets with liquid nitrogen.

3. The product of claim 2 wherein the thermoplastic polymer is high density polyethylene.

4. The product of claim 1 wherein in the process, the process includes adding a gaseous or liquid blowing agent during the step (i) of co-extruding.

5. The product of claim 4 wherein the thermoplastic polymer is high density polyethylene.

6. The product of claim 1 wherein the thermoplastic polymer is high density polyethylene.

* * * * *